United States Patent [19]

Fogt et al.

[11] Patent Number: 4,906,249
[45] Date of Patent: Mar. 6, 1990

[54] TERPOLYMER COMPOSITION WITH BOUND INDICATOR DYE FOR FIBER OPTIC PROBE

[75] Inventors: Eric Fogt, Maple Grove; Linda Cahalan, Champlin; Cheryl Feia, St. Paul; Jeff Schweitzer, St. Anthony; Pat Cahalan, Champlin, all of Minn.

[73] Assignee: Medtronic, Inc., Minneapolis, Minn.

[21] Appl. No.: 314,561

[22] Filed: Feb. 23, 1989

[51] Int. Cl.$^4$ .................. C09B 69/10; C09B 67/00; A61B 5/00
[52] U.S. Cl. ........................... 8/647; 8/555; 252/408.1; 525/328.2; 128/634; 128/636
[58] Field of Search .............. 8/647, 555; 525/328.2; 252/408.1; 128/634, 636

[56] References Cited

U.S. PATENT DOCUMENTS

| | | | |
|---|---|---|---|
| 4,101,269 | 7/1978 | Champenois | 8/647 |
| 4,132,841 | 1/1979 | Champenois | 8/647 |
| 4,194,877 | 3/1980 | Peterson et al. | |
| 4,200,110 | 4/1980 | Peterson et al. | |
| 4,476,870 | 10/1984 | Peterson et al. | |
| 4,622,356 | 11/1986 | Jarovitzky et al. | 525/328.2 |
| 4,801,655 | 1/1989 | Murray, Jr. et al. | 8/555 |

OTHER PUBLICATIONS

Hiroo Tanaka, Copolymerization of Cationic Monomers with Acrylamide in an Aqueous Solution, Journal of Polymer Sci., Pol. Chem. Ed., vol. 24, 29-36, 1986.
McCormick, C., et al. Water-Soluble Copolymers ..., Journal of Polymer Sci., Pol. Chem. Ed., vol. 22, 49-60, 1984.
Fiber-Optic Probe for Intravascular Blood Gas Monitoring, submitted to Univ. of Minn., 11-88, Jeffrey A. Schweitzer.
Fiber Optic pH Probe for Physiological Use by Peterson and Buckhold, Analytical Chemistry, vol. 52, No. 6, May 1980, at pp. 864-869.
Performance of an In-vivo, Continuous Blood-Gas Monitor with Disposable Probe, by William W. Miller et al, in Clin. Chem., 33/9, 1538-1542 (1987).

Primary Examiner—Dennis Albrecht
Assistant Examiner—Jeff Darland
Attorney, Agent, or Firm—Vidas & Arrett

[57] ABSTRACT

An improved pH probe based on fiber optics and a unique cross-linked terpolymer of methacrylamidopropyl-trimethyl ammonium chloride, sodium acrylamidopropane sulfonate, and acrylamide, the terpolymer having bound thereto an indicator dye.

12 Claims, 1 Drawing Sheet pH VERSES IONIC STRENGTH

○ GLASS ELECTRODE
▲ PRIOR ART
● INVENTION

TERPOLYMER COMPOSITION WITH BOUND INDICATOR DYE FOR FIBER OPTIC PROBE

BACKGROUND OF THE INVENTION

Field of the Invention and Description of the related art

Non-electrical pH probes and pO2 probes based on fiber optics and a dye indicator are known. Such devices are described fully in an article entitled "Fiber Optic pH Probe for Physiological Use" by Peterson and Buckhold which appeared in *Analytical Chemistry*, Vol 52, No. 6, May 1980 at pp. 864-869 and in a thesis entitled A Fiber-Optic Probe For Intravascular Blood Gas Monitoring submitted to the University of Minnesota in November 1988 by Jeffrey A. Schweitzer. These devices and compositions used in them are also described in U.S. Pat. Nos. 4,194,877; 4,200,110 and 4,476,870. All of these references are incorporated herein by reference.

This type of probe is based on the color change an indicator dye undergoes with varying conditions. For example, in a pH probe using phenol red, the dye exists in two forms over a certain pH range, exhibiting two different light absorption spectra. As the pH of a solution to which the probe is exposed varies, the optical absorbance varies in proportion to the change in pH. Operation is based on optically detecting the color change of the dye by fiber optic means as pH varies.

Heretofore, the indicator dye has been bound to an acrylic polymer composition, the dye being present with the monomer during the polymerization procedure. This prior art composition is referred to herein generally as a "acrylamide homopolymer". Unfortunately, the acrylamide homopolymer compositions have not been as stable as desired and have exhibited undesirable drift in pH indication and inaccurate indication over various ionic strength ranges. It is an object of this invention to provide a polymer dye composition which is improved in respect to these characteristics.

SUMMARY OF THE INVENTION

The improved polymer dye compositions of this invention include substantially equal amounts of an anionic monomer and cationic monomer, a lesser amount of a neutral monomer and a cross linking agent along with a dye of the aforementioned type which is covalently bound to the resultant trimonomer copolymer without a loss of its pH indicator function. These composition are referred to herein generally as "trimonomer copolymer" compositions.

DESCRIPTION OF THE PREFERRED EMBODIMENTS

Figure 1:
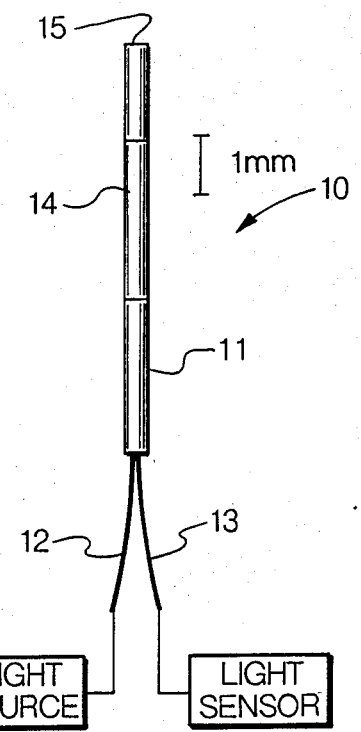
FIG. 1 is a view of the distal end of a fiber optic pH probe.

Referring to FIG. 1, there is shown a fiber optic pH probe 10 which includes an ion permeable membrane envelope 11 enclosing the distal ends of a pair of optical fibers 12 and 13. Envelope 11 may be in tubular form as shown fitting closely about the two fibers 12 and 13. Retained within envelope 11 and distal to the ends of fiber 12 and 13 is a pH-indicating dye-containing composition 14 of the invention. A suitable sealing material such as, for example, ultraviolet light setting optical cement 15, is employed to seal the distal end of envelope 11 after composition 14 has been included in envelope 11. Such sealing material may also be employed where optical fibers 12 and 13 enter envelope 11 to hold the assembly together. The structure of the probe may be the same as that shown in U.S. Pat. No. 4,200,110.

Cuprophane B4AH, a regenerated cellulose material in the form of dialysis tubing having for example an inner diameter of 300 microns and a wall thickness of 19 microns is an acceptable cylindrical material for use as envelope 11. It is ion permeable but does not allow passage of the dye composition. Other suitable materials may also be used.

The dye used may be any dye indicator which can be bound to the polymeric composition without loss of its indicator function. The types mentioned in the prior art are acceptable. Phenol red is preferred, particularly for PH indication. Others, such as brilliant yellow C124890 (Eastman 837) and rosolic acid CI43800 (Matheson Coleman and Bell RX1801NB401), may be used also.

The trimonomer copolymer compositions to which the dye is bound include substantially equal relative amounts of an anionic monomer constituent and a cationic monomer constituent and a minor amount of a neutral monomer constituent. The constituents are copolymerized together with a cross linking agent in the presence of the dye to form the copolymer composition of the invention including the bound dye i.e., to form a dye-containing cross linked trimonomer copolymer composition.

The most preferred anionic monomer constituent is acrylamido-propane sulfonate (AMPS). Other anionic monomers such as acrylic acid and its derivatives may be used.

The most preferred cationic monomer constituent is methacrylamidopropyl-trimethylammonium chloride (MAPTAC). Other cationic monomers such as aminoethyl methacrylate and its derivatives may be used.

The most preferred neutral monomer is acrylamide monomer. Other neutral monomers such as hydroxyalkyl methacrylates and acrylamide derivatives may be used. The preferred cross linking agent is methylenebisacrylamide (MBA).

The dye-containing trimonomer copolymer compositions of this invention in preferred form are as follows:

| NaAmps/MAPTAC (Equal Amts in Copolymer Wt % | Acrylamide Wt % | Dye Wt % |
| --- | --- | --- |
| 93.1 | 4.9 | 2 ± 1 |
| 88.2 | 9.8 | 2 ± 1 |
| 78.4 | 19.6 | 2 ± 1 |

Even less than about 1% by weight dye may be included. An overall range is about 0.1%-3%, about 1-2% being most preferred.

The following examples are illustrative of the preparation of various compositions of the invention.

EXAMPLE 1

| Material (Starting Amounts) | |
| --- | --- |
| water (DI) | 48 ml. |
| MAPTAC | 28.8 g |
| NaAMPS | 28.8 g |
| Acrylamide | 3.2 g |
| MBA (methylenebis-acrylamide) | 1.0 g |
| Phenol Red | 0.38 g |
| $K_2S_2O_8$ | 2 ml. at 2% soln. ⎫ |
| $K_2S_2O_3$ | 2 ml. at 2% soln. ⎬ Catalysts |
| $F_eSO_4$ | 2 ml. at 1% soln. ⎭ |

Procedure

Mix the three monomers together with deionized (DI) water. Add the MBA and stir with magnetic stir bar until dissolved. Add the phenol red and stir until dissolved. Prepare 10 ml. of each catalyst constituent (fresh daily). Bubble the solution for about 15 minutes with nitrogen. Insert a thermometer to monitor temperature. Add all three catalysts (using a syringe to dispense each) simultaneously while stirring the solution. Monitor temperature and record when the solution gels enough to stop the stir bar.

Wash and Dry

Prepare a wash solution of 50 wt % DI $H_2O$ and 50 wt % ethanol mixed together. Rinse composition until filtrate is clear—10 washes typical. Dry composition with a final wash of pure ethanol and place in a vacuum oven at 50° C. overnight. When dry, grind into powder.

The resultant copolymer portion of the composition is about 90% equal amounts of anionic/cationic constituent and about 10% of neutral constituent, in relative amounts. The overall composition also includes about 1-2% of bound dye.

EXAMPLE 2

| Materials (Starting Amounts) | |
| --- | --- |
| water (DI) | 45 ml. |
| MAPTAC | 30.0 g |
| NaAMPS | 30.0 g |
| Acrylamide | 2.0 g |
| MBA | 1.0 g |
| Phenol red | 0.38 g |
| $K_2S_2O_8$ | 2 ml. at 2% soln. ⎫ |
| $K_2S_2O_3$ | 2 ml. at 2% soln. ⎬ Catalysts |
| $F_eSO_4$ | 2 ml. at 1% soln. ⎭ |

Procedure and Wash/Dry—Same as Example 1

The resultant copolymer portion of the composition is about 95% equal amounts of anionic/cationic constituent and about 5% of neutral constituent, in relative amounts. The overall composition also includes about 1-2% of bound dye.

EXAMPLE 3

| Materials (Starting Amounts) | |
| --- | --- |
| water (DI) | 50 ml. |
| MAPTAC | 25.6 g |
| NaAMPS | 25.6 g |
| Acrylamide | 6.4 g |
| MBA | 1.0 g |
| Phenol red | 0.38 g |
| $K_2S_2O_8$ | 2 ml. at 2% soln. ⎫ |
| $K_2S_2O_3$ | 2 ml. at 2% soln. ⎬ |
| $F_eSO_4$ | 2 ml. at 1% soln. ⎭ |

Procedure and Wash/Dry—Same as Example 1

The resultant copolymer portion of the composition is about 80% equal amounts of anionic/cationic constituents and about 20% neutral constituent, in relative amounts. The overall composition also include about 1-2% of bound dye.

EXAMPLE 4

| Materials (Starting Amounts) | |
| --- | --- |
| Water (DI) | 45 ml |
| MAPTAC | 30.0 g |
| NaAMPS | 30.0 g |
| Acrylamide | 2.0 g |
| MBA | 1.0 g |
| Phenol red | 0.38 g |
| $(NH_4)_2S_2O_8$ | 3.8 g ⎫ catalysts |
| $FeSO_4$ | 2 ml of 1% soln. ⎭ |

Procedure and WashDry—Same as previous Examples

The resultant copolymer portion of the composition is about 95% equal amounts anionic/cationic constituent and about 5% neutral constituent, in relative amounts. The overall composition also includes about 1-2% of bound dye.

EXAMPLE 5

| Materials (Starting Amounts) | |
| --- | --- |
| $H_2O$ (DI) | 45 ml |
| MAPTAC | 30.0 g |
| NaAMPS | 30.0 g |
| Acrylamide | 2.0 g |
| MBA | 0.7 g |
| Phenol red | 0.38 g |
| $(NH_4)_2S_2O_8$ | 3.8 g |
| $FeSO_4$ | 1 ml of 0.5% soln. catalyst |
| $K_2S_2O_8$ | 2 ml. at 2% soln. ⎫ |
| $K_2S_2O_3$ | 2 ml. at 2% soln. ⎬ Catalysts |
| $F_eSO_4$ | 2 ml. at 1% soln. ⎭ |

Procedure and Wash Dry—same as previous Examples

The resultant copolymer portion of the composition is about 95% equal amounts of anionic/cationic constituent and about 5% neutral constituent in relative amounts. The overall composition also includes about 1-2% of bound dye.

STABILITY COMPARISON

The table below compares a powder of the Example 1 composition to a typical prior art acrylamide hompolymer composition of the type described in U.S. Pat. Nos. 4,200,110 and 4,194,877, both using phenol red dye for the purpose of comparing stability when each of the powders are incorporated into a probe.

Test 1 was started less than 8 hours after initial hydration. Test 2 was started after storage on 7.4 buffer at 55° C. for 14 days. Samples of each composition were tested for drift of pH sensed over time.

TABLE

| Sample | TEST #1 Drift pH Units/day | TEST #2 Drift pH Units/day |
| --- | --- | --- |
| Prior Art Composition (acrylamide homopolymer) | −0.090 | −0.017 |
| Composition of invention (trimonomer copolymer) | −0.025 | −0.005 |

The compositions of the invention appear to have about twice the sensitivity as the prior art compositions, based or absorbance measurements made on fabricated probes. This is believed to be due to the fact that the compositions of the invention contain greater amounts of retained dye.

Figure 2:
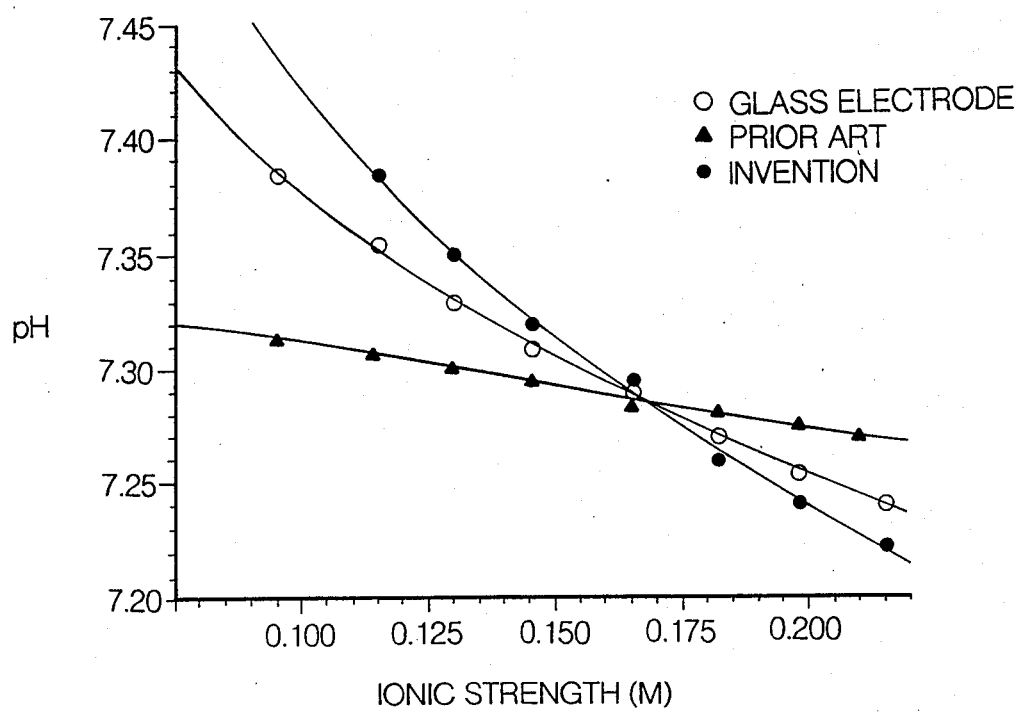
FIG. 2 is a graph showing the improved accuracy of a probe using a typical composition of the invention compared to a prior art probe and compositions of the type shown in U.S. Pat. Nos. 4,200,110 and 4,194,877. The data being plotted in terms of pH versus ionic strength.

FIG. 2 shows pH response of a standard glass electrode, a homopolymer probe of the prior art (structure as FIG. 1), all plotted to varying ionic strengths. The copolymer probe response is similar to that of the glass electrode. The response of the homopolymer probe is affected by the ionic strength of the sample resulting in less accurate pH measurement.

The invention and its attendant advantags will be understood from the foregoing description and will be apparent that various changes may be made without departing from the spirit and scope of the invention. The forms described herein are merely preferred embodiments of the invention.

This completes the description of the preferred embodiments of the invention. Those skilled in the art may recognize other equivalents to the specific embodiments described herein which equivalents are intended to be encompassed by the claims attached thereto.

What is claimed is:

1. As a composition of matter, a cross-linked trimonomer copolymer consisting essentially of methacrylamidopropyl-trimethyl ammonium chloride (MAPTAC), sodium acrylamidopropane sulfonate (NaAMPS) and acrylamide, the copolymer having bound thereto an indicator dye.

2. The composition of claim 1 in which the indicator dye is phenol red.

3. The composition of claim 1 in which the cross-linking agent is methylenebisacrylamide (MBA).

4. The composition of claim 1 in which the dye is a pH indicator type.

5. The composition of claim 1 in which the copolymer is composed of substantially equal quantities of methaacrylamidopropyl-trimethyl ammonium chloride (MAPTAC) and sodium acrylamidopropane sulfonate (NaAmps) together in predominant amount, the acrylamide being included in lesser amount.

6. The composition of claim 5 in which the substantially equal amouns of methaacrylamidopropyl-trimethyl ammonium chloride (MAPTAC) and sodiumacrylamidopropane sulfonate (NaAmps) are present in an amount together of 80-95% by weight in the copolymer and the acrylamide is present in an amount of about 20-5% by weight.

7. The composition of claim 6 in which the stated amounts are about 90% and 10%, respectively.

8. The composition of claim 6 in which the stated amounts are about 95% and 5%, respectively.

9. The composition of claim 1 in which the amount of dye bound to the copolymer is from about 0.1% to about 3% by weight.

10. The composition of claim 1 in which the amount of dye bound to the copolymer is about 1-2% by weight.

11. The composition of any one of the preceding claims in the combination with a fiber optic probe.

12. The composition of claim 11 in which the probe is a pH probe.

* * * * *

UNITED STATES PATENT AND TRADEMARK OFFICE
CERTIFICATE OF CORRECTION

PATENT NO. : 4,906,249
DATED : March 6, 1990
INVENTOR(S) : Eric Fogt et al

It is certified that error appears in the above-identified patent and that said Letters Patent is hereby corrected as shown below:

Col. 5, line 23, delete "advantags" and insert - advantages -

Col. 6, line 17, delete "amouns" and insert - amounts -

Signed and Sealed this

Fifteenth Day of January, 1991

*Attest:*

HARRY F. MANBECK, JR.

*Attesting Officer*  *Commissioner of Patents and Trademarks*